United States Patent [19]

Jung et al.

[11] 3,997,595

[45] Dec. 14, 1976

[54] 2-CHLOROETHANEPHOSPHONIC ACID DERIVATIVES

[75] Inventors: Johann Jung, Limburgerhof; Karl Kiehs, Lampertheim; Hans Theobald, Limburgerhof, all of Germany

[73] Assignee: BASF Aktiengesellschaft, Ludwigshafen (Rhine), Germany

[22] Filed: Feb. 12, 1975

[21] Appl. No.: 549,332

[30] Foreign Application Priority Data

Feb. 23, 1974 Germany ............................ 2408863

[52] U.S. Cl. .............................. 260/502.5; 71/86; 71/87; 260/239 ER; 260/243 R; 260/247; 260/293.51; 260/326.61; 260/543 P; 260/551 P; 260/959

[51] Int. Cl.² .......................................... C07F 9/38

[58] Field of Search ............................ 260/502.5

[56] References Cited

UNITED STATES PATENTS

| | | | |
|---|---|---|---|
| 2,670,369 | 2/1954 | Filatoff-Rocq et al. | 260/502.5 |
| 2,765,276 | 10/1956 | Winkle et al. | 260/502.5 |
| 3,223,514 | 12/1965 | Gradsten | 260/502.5 |
| 3,493,639 | 2/1970 | Taus | 260/502.5 |
| 3,775,470 | 11/1973 | Vogel | 260/502.4 R |
| 3,787,486 | 1/1974 | Randall et al. | 260/502.4 R |
| 3,799,758 | 3/1974 | Franz | 260/502.5 |
| 3,901,679 | 8/1975 | Hofer et al. | 260/502.5 |

*Primary Examiner*—Joseph E. Evans
*Attorney, Agent, or Firm*—Johnston, Keil, Thompson & Shurtleff

[57] ABSTRACT

New and valuable 2-chloroethane-phosphonic acid derivatives having a strong biological action, agents for controlling the growth of plants containing these compounds as active ingredients, a process for influencing the growth of plants with these compounds, and a process for their preparation.

1 Claim, No Drawings

2-CHLOROETHANEPHOSPHONIC ACID DERIVATIVES

This application discloses and claims subject matter described in German Patent Application No. P 24 08 863.9, filed Feb. 23, 1974, which is incorporated herein by reference.

The present application relates to new 2-chloroethanephosphonic acid derivatives, agents containing them for controlling plant growth, a process for producing these compounds, and a process for regulating plant growth.

It is known (Dutch Patent Application No. 6,802,633, British Pat. No. 1,194,433, and German Laid-Open Applications DOS No. 1,667,968; 2,140,842; and 1,950,099) that 2-chloroethanephosphonic acid and their reaction products with imines and primary amines have growth regulating properties.

We have now found that 2-chloroethanephosphonic acid derivatives of the formula

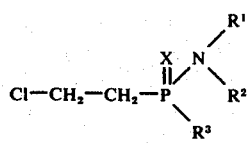

where X denotes oxygen or sulfur, $R^1$ and $R^2$ each denote lower alkyl of a maximum of 6 carbon atoms, or $R^1$ and $R^2$, together with the nitrogen atom, form a heterocyclic ring of 2 to 7 carbon atoms, e.g., unsubstituted or alkyl- or halogen-substituted morpholine, thiomorpholine, piperidine and pyrrolidine, and $R^3$ denotes halogen, hydroxyl, monoalkylamino of 1 to 6 carbon atoms, monophenylamino which may be substituted by halogen, nitro, hydroxy or alkyl, $R^3$ further denotes alkyloxy or alkylthio of a maximum of 6 carbon atoms, or phenyloxy or phenylthio which may be substituted by halogen, nitro, hydroxy or alkyl, have a strong influence on plant growth.

The compounds of the invention may be prepared for instance by the following methods:

substituted by halogen, nitro or alkyl. As the compounds of the formula IV need not be isolated in the preparation of compounds of the formulae VI and VIII, a single-vessel process may be used. The compounds of the formulae VI and VIII may also be prepared by stagewise reaction of compounds of the formula II first with equimolar amounts of compounds of the formulae V and VII, and then with the secondary amines of the formula III. The intermediates of the formulae IX and X, in which X and $R^4$ have the above meanings, need not be isolated:

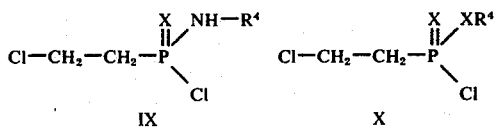

These reactions are therefore advantageously carried out in a single vessel.

The hydrogen chloride liberated in the above reactions may be removed from the reaction mixture for instance by means of inert gas, e.g., dry nitrogen, or intercepted with a tertiary amine, e.g., triethylamine, by reaction of an alkali metal or alkaline earth metal carbonate or hydrocarbonate, by using twice the molar amount of amines of the formulae II and VII, or by using alkali metal salts of the alcohols of the formula V.

The above reactions are advantageously carried out in solvents. Examples of suitable solvents are benzene and substituted benzenes, e.g., toluene, xylenes and chlorobenzenes, nitriles, e.g., acetonitrile and propionitrile, ethers, e.g., diethyl ether, dioxane, hydrocarbons, chlorinated hydrocarbons, e.g., methylene chloride, chloroform and carbon tetrachloride, ketones, e.g., acetone and methyl ethyl ketone, and other inert solvents. Reaction temperatures are from $-10°$ to $+100°$ C.

The following examples demonstrate the preparation of the compounds of the invention.

EXAMPLE 1

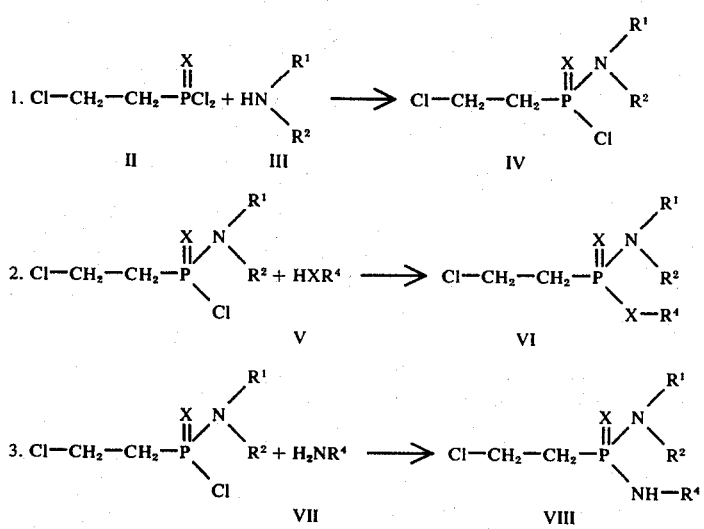

In the formulae II to VIII, $R^1$, $R^2$ and X have the meanings given in formula I, and $R^4$ denotes hydrogen, alkyl of 1 to 6 carbon atoms, or phenyl which may be At 10° to 20° C, 180 parts (by weight) of dimethylamine was dripped into 363 parts of 2-chloroethanephosphonic dichloride dissolved in 1,500 parts of absolute benzene. The mixture was then stirred for 4 hours at 60° C. After the mixture had been cooled, the precipitated dimethylamine hydrochloride was separated. The filtrate was freed from solvent in vacuo and the liquid residue distilled at 87° to 90° C (0.1 mm Hg). There was obtained 345 parts ($\triangleq$ 91% of theory) of 2-chloroethanephosphonic monodimethylamidomonochloride of the formula

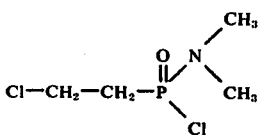

$n_D^{25} = 1.4904$ $C_4H_{10}NPOCl_2$ (190): Calc.: C 25.3 H 5.3 N 7.4 P 16.3 Cl 37.4; Found: C 25.4 H 5.1 N 7.1 P 16.9 Cl 37.3

The following compounds were prepared analogously:

EXAMPLE 2

At 20° C, 137 parts of 2-chloroethanephosphonic monomorpholinomonochloride was dripped into 500 parts of water. The mixture was then stirred for 2 hours at 80° C, treated with animal black and filtered. The excess water was removed in vacuo and the product heated at 60° C (0.1 mm Hg) until constant weight was reached. The compound was then dried over $P_2O_5$ and NaOH. There was obtained 125 parts ($\triangleq$ 100% of theory) of 2-chloroethanephosphonic monomorpholide of the formula

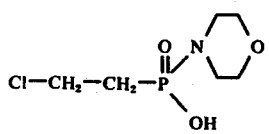

$C_6H_{13}NPO_3Cl$ (213.5): Calc.: C 37.7 H 6.1 N 6.6 P 14.5 Cl 16.6; Found: C 37.9 H 5.9 N 6.8 P 14.7 Cl 17.1

The following compounds were prepared analogously:

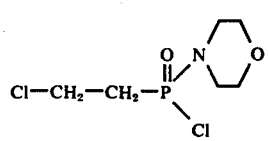
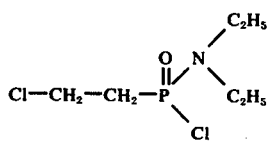

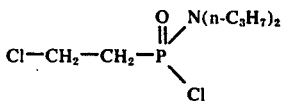
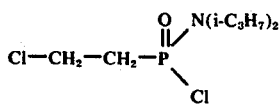

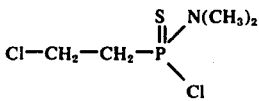
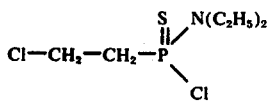

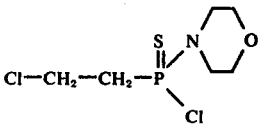
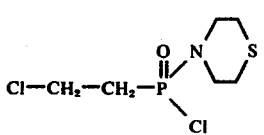

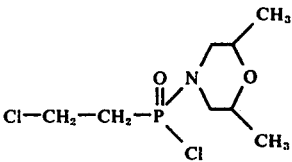
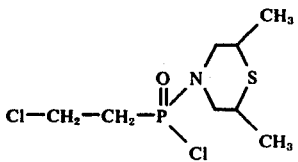

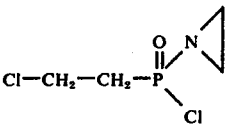
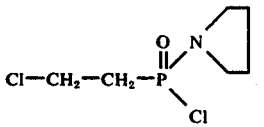

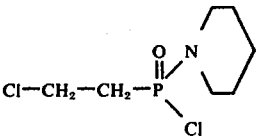
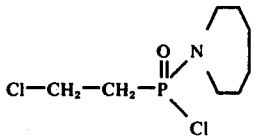

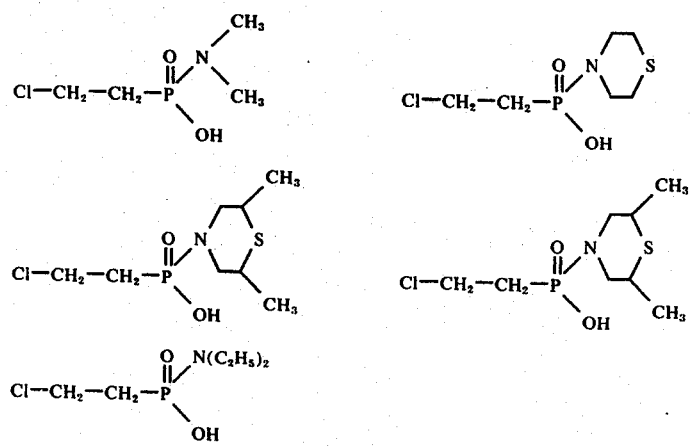

EXAMPLE 3

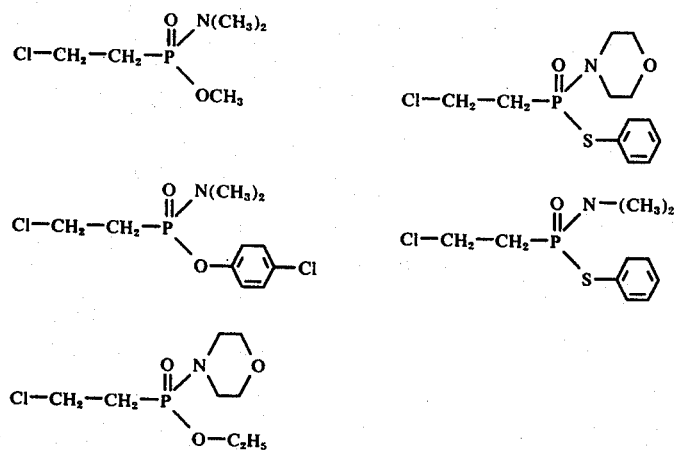

At 10° C, a solution of 11 parts of thiophenol in 50 parts of absolute benzene was added dropwise to a solution of 20.6 parts of 2-chloroethanethiophosphonic monodimethylamidomonochloride in 100 parts of absolute benzene. Subsequently, 10.1 parts of triethylamine in 50 ml of absolute benzene was dripped in at 10° C. The mixture was then stirred for 30 minutes at 20° C and for 1 hour at 60° C. The precipitated triethylamine hydrochloride was suction filtered and the filtrate treated three times with three different 20 cm³ portions of 10 wt% aqueous NaHCO₃ solution and then dried over Na₂SO₄. The solvent was removed in vacuo and the oily residue heated at 60° C (0.1 mm Hg) until constant weight was reached. The yield was 24 parts (≙ 81% of theory) of

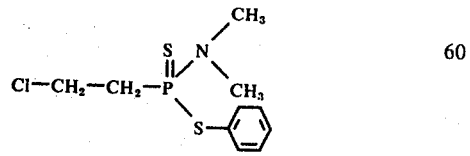

$C_{10}H_{15}ClNPS_2$ (279.5): Calc.: C 43.0 H 5.4 N 5.0 P 11.1 S 22.9 Cl 12.7; Found: C 43.3 H 5.5 N 5.2 P 11.6 S 23.3 Cl 12.8

The following compounds were prepared analogously:

EXAMPLE 4

At 0° to 10° C, a solution of 5.9 parts of isopropylamine in 50 parts of absolute ether was added to a solution of 13.8 parts of 2-chloroethanephosphonic monodimethylthiomorpholinomonochloride in 15 parts of absolute ether. The mixture was then stirred for 1 hour at room temperature and for 3 hours at 35° C. Subsequently, the precipitated isopropylamine hydrochloride was removed by suction filtration and the filtrate extracted with 10 wt% aqueous NaHCO₃ solution and dried over Na₂SO₄. The solvent was then removed in vacuo and the oil which remained was heated at 60° C (0.1 mm Hg) until constant weight was reached. The yield was 13 parts (88% of theory) of

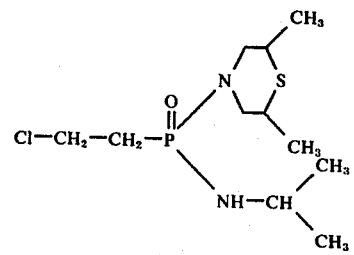

$C_{11}H_{24}ClN_2OPS$ (298.5): Calc.: C 44.2 H 8.0 N 9.4 P 10.4 S 10.7; Found: C 44.0 H 7.9 N 9.5 P 10.0 S 10.1

The following compounds were prepared analogously:

The new compounds have the following physical properties: refractive index ($n_D^{25}$), nuclear resonance spectra (60 MHz δ values) or infrared spectra (characteristic values (cm$^{-1}$)).

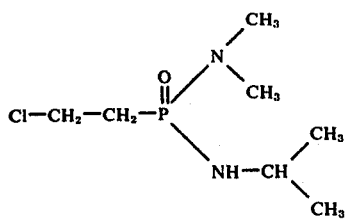
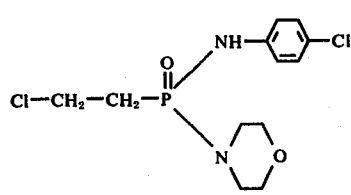
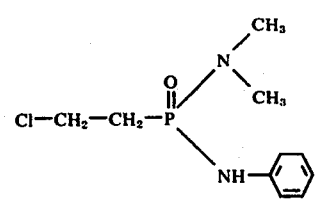
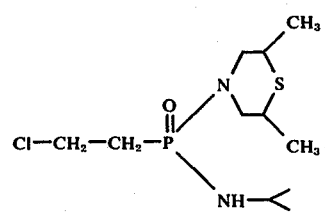
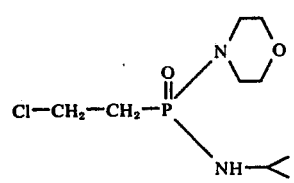

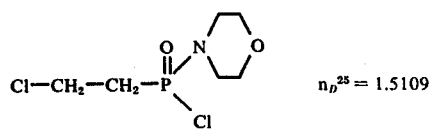   $n_D^{25} = 1.5109$

| | 60 MHz NMR / δ values | characteristic infrared values (cm$^{-1}$) |
|---|---|---|
| Cl—CH₂—CH₂—P(O)(Cl)—N(morpholine with 2,6-CH₃, S) | 1.0-1.5 (6H), 3.4-4.05 (2H)<br>2.2-3.4 (8H) | |
| Cl—CH₂—CH₂—P(O)(Cl)—N(thiomorpholine) | 3.9 (2H), 2.8 (2H),<br>3.3-3.8 (4H), 2.5-3.0 (4H) | |
| Cl—CH₂—CH₂—P(O)(Cl)—N(piperidine) | 3.85 (2H), 2.72 (2H),<br>3.2 (4H), 1.67 (6H) | |
| Cl—CH₂—CH₂—P(O)(Cl)—N(2,6-dimethylmorpholine) | 1.1-1.4 (6H), 2.1-4.05 (10H) | |

-continued
| | 60 MHz NMR / δ values | characteristic infrared values (cm⁻¹) |
|---|---|---|
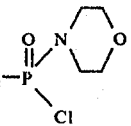  $n_D^{25} = 1.5109$
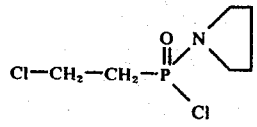  3.90 (2H), 2.72 (2H), 3.15-3.4 (4H), 3.95 (4H)
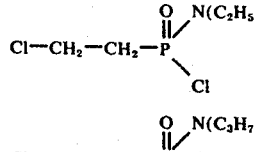  1240, 1020, 520
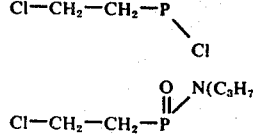  1240, 1010, 740, 520
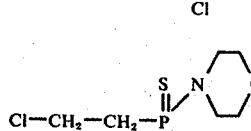  1270, 1020, 530
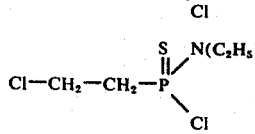  1110, 960, 790, 740
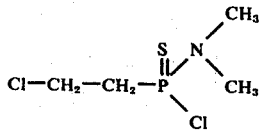  1150, 1015, 790, 750, 615
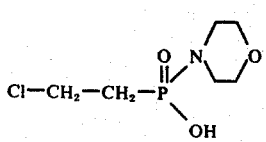  1160, 980, 800, 750, 610
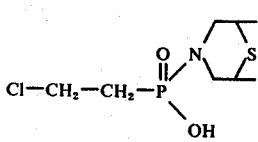  2.35 (2H), 3.82 (2H), 3.30 (4H), 3.95 (4H)
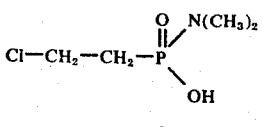  4.30 (2H), 3.78 (2H), 1.1-1.45 (6H), 2.7-3.65 (6H)
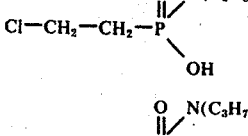  1600, 1300, 1150, 980, 940, 500
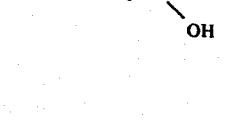  1600, 1310, 1150, 980, 940, 500
1600, 1310, 1150, 980, 940, 500

-continued

| structure | 60 MHz NMR / δ values | characteristic infrared values (cm⁻¹) |
|---|---|---|
| Cl—CH₂—CH₂—P(=O)(N-morpholino)(Cl) | $n_D^{25} = 1.5109$ | |
| Cl—CH₂—CH₂—P(=O)(N(C₃H₇-i)₂)(OH) | | 1600, 1300, 1160, 990, 935, 510 |
| Cl—CH₂—CH₂—P(=O)(N-thiomorpholino)(OH) | | |
| Cl—CH₂—CH₂—P(=O)(N-morpholino)(O-C₆H₅) | 2.45 (2H), 3.7 (2H), 2.9-3.3 (4H), 3.3-3.7 (4H), 6.7-7.5 (5H) | |
| Cl—CH₂—CH₂—P(=O)(N(CH₃)₂)(O-C₆H₅) | 2.4 (2H), 3.8 (2H), 3.6 (6H), 6.7-7.3 (5H) | |
| Cl—CH₂—CH₂—P(=O)(N(CH₃)₂)(O-C₆H₄-Cl) | | 1200, 1090, 980, 900, 820 |
| Cl—CH₂—CH₂—P(=O)(N-morpholino)(S-C₆H₅) | | 1210, 1110, 960, 750, 700, 550 |
| Cl—CH₂—CH₂—P(=O)(N-morpholino)(OCH₃) | | 1230, 1110, 1030, 970, 810 |
| Cl—CH₂—CH₂—P(=O)(N(CH₃)₂)(S-C₆H₅) | | 1280, 1160, 980, 750, 610 |
| Cl—CH₂—CH₂—P(=O)(N(CH₃)₂)(NH—CH(CH₃)₂) | 2.2 (2H), 3.1-4.1 (3H), 2.7 (6H), 1.1-1.6 (6H) | |

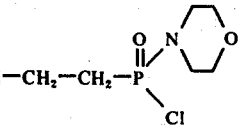

$n_D^{25} = 1.5109$

| | 60 MHz NMR / δ values | characteristic infrared values (cm⁻¹) |
|---|---|---|
| 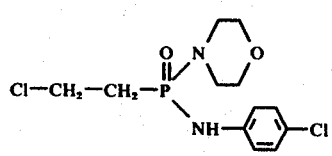 | 2.4 (2H), 3.7 (2H), 2.8-4.5 (4H), 3.4-3.7 (4H), 6.7-7.3 (5H) | |
| 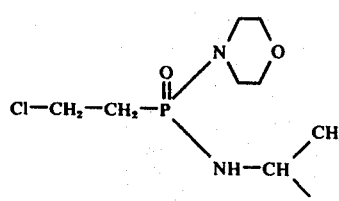 | 2.3 (2H), 3.8 (2H), 2.9-3.55 (4H), 3.6-3.8 (4H), 1.0-1.5 (6H) | |
| 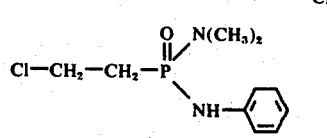 | | 1290, 1190, 1000, 930, 750, 700 |
| 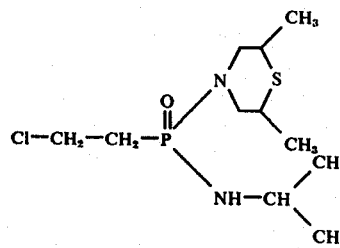 | | 1170, 1010, 900 |

The agents according to the invention may be used as solutions, emulsions, suspensions, dusts or granules. The forms of application depend entirely on the purpose for which the agents are being used; in any case they should ensure a fine distribution of the active ingredient.

For the preparation of solutions to be sprayed direct, the solution in water is suitable. However, there may also be used as spray liquids hydrocarbons having boiling points above 150° C, e.g., tetrahydronaphthalene and alkylated naphthalenes, and organic liquids having boiling points above 150° C and one or more functional groups, e.g., the keto, ether, ester and amide groups, this group or these groups being attached as substituent(s) to a hydrocarbon chain or being (a) component(s) of a heterocyclic ring. Natural vegetable oils such as palm oil are also often suitable.

Aqueous formulations may be prepared from concentrates, pastes or wettable powders by adding water. To prepare emulsions, the ingredients as such or dissolved in a solvent may be homogenized in organic solvents by means of wetting or dispersing agents, e.g., polyethylene oxide adducts. Concentrates which are suitable for dilution with water may be prepared from active ingredient, wetting agent, adherent, emulsifying or dispersing agent and possibly solvent.

Dusts may be prepared by mixing or grinding the active ingredients with a solid carrier, e.g., talc, clay, kieselguhr and fertilizers.

The main characteristic of the new compounds is that they have an intensive growth-reducing action on plants, e.g., cereals. The main standard for assessing the intensity of the action is the degree of stunt, but other morphological changes are also taken into account which are encompassed by the term "epinasty". These nastic movements involve a bending or a curling of the leaves round the shoot of the plant, and may be considered to be an expression of the biological activity of a phosphonic acid derivative. The reduction in growth height and the degree of epinasty are also an indication of other plant growth responses e.g., increase in branching and tillering, root stimulation, induction of flowering (e.g., in Bromeliaceae), hastening or inhibiting flowering and ripening (e.g., in tomatoes and grapes), and influencing metabolism and the production of various plant substances (e.g., promotion of latex flow in Hevea).

The following examples demonstrate the action of the compounds according to the invention.

EXAMPLE 5

Cress seeds are placed on moist filter paper and, because the seeds adhere to the paper, it is arranged in an upright position in a beaker containing 20 ml of an aqueous active ingredient solution. After 4 days the length of the cress seedlings is measured and the percentage growth height compared with the untreated control is calculated therefrom.

| Active ingredient concentration: 20 ppm | Growth height in % | |
|---|---|---|
| Active ingredient | shoot | whole plant |
| untreated (control) | 100 | 100 |
| Cl—CH$_2$—CH$_2$—P(=O)(OH)(OH) (prior art) | 33.2 | 41.6 |
| Cl—CH$_2$—CH$_2$—P(=O)(N(CH$_3$)(CH$_3$))(Cl) | 23.8 | 36.5 |

EXAMPLE 6

Indian corn plants growing in pots are sprayed at a growth height of 22 cm with aqueous solutions of the active ingredients; the application rate is 10 mg of active ingredient per pot, corresponding to 3 kg/ha. For the next 8 weeks the plants grow in the open. The length of the plant parts above the soil is then measured.

| Active ingredient | Plant height cm | relative |
|---|---|---|
| untreated (control) | 111.3 | 100 |
| Cl—CH$_2$—CH$_2$—P(=O)(OH)(OH) (prior art) | 108.3 | 97.3 |
| Cl—CH$_2$—CH$_2$—P(=O)(N(CH$_3$)(CH$_3$))(Cl) | 103.5 | 93.0 |
| Cl—CH$_2$—CH$_2$—P(=O)(N(C$_2$H$_5$)(C$_2$H$_5$))(Cl) | 98.3 | 88.3 |

EXAMPLE 7

90 parts by weight of the compound of Example 1 is mixed with 10 parts by weight of N-methyl-α-pyrrolidone. A mixture is obtained which is suitable for application in the form of very fine drops.

EXAMPLE 8

20 parts by weight of the compound of Example 2 is dissolved in a mixture consisting of 80 parts by weight of water, 10 parts by weight of the adduct of 8 to 10 moles of ethylene oxide to 1 mole of oleic acid-N-monoethanolamide, 5 parts by weight of the calcium salt of dodecylbenzenesulfonic acid, and 5 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 9

20 parts by weight of the compound of Example 1 is dissolved in a mixture consisting of 70 parts by weight of water, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 10

3 parts by weight of the compound of Example 1 is intimately mixed with 97 parts by weight of particulate kaolin. A dust is obtained containing 3% by weight of the active ingredient.

EXAMPLE 11

30 parts by weight of the compound of Example 2 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE 12

A grass seed mixture provided with sufficient nutrients was allowed to grow in glass vessels for 17 days. The grass blades were then cut to a height of about 2 cm and sprayed 3 days later with aqueous formulations of the following active ingredients.

The height of the lawn was measured 14 days after this treatment.

| Active ingredient | Amount applied in kg/ha | Lawn height cm | relative |
|---|---|---|---|
| untreated | — | 13.8 | 100 |
| Cl—CH$_2$—CH$_2$—P(=O)(OH)(OH) (prior art) | 1.5 | 11.0 | 79.7 |
|  | 6 | 10.0 | 72.5 |
| Cl—CH$_2$—CH$_2$—P(=O)(N(CH$_3$)(CH$_3$))(OH) | 1.5 | 10.0 | 72.5 |
|  | 6 | 9.0 | 65.2 |

EXAMPLE 13

Potatoe plants were sprayed at a height of about 10 cm with aqueous formulations of the active ingredients. After 25 days, the height of the plants was measured.

| Active ingredient | Amount applied in kg/ha | Growth height cm | relative |
|---|---|---|---|
| untreated | — | 38.0 | 100 |

-continued
| Active ingredient | Amount applied in kg/ha | Growth height cm | relative |
|---|---|---|---|
| 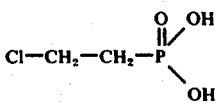 (prior art) | 6 | 18.0 | 47.4 |
-continued
| Active ingredient | Amount applied in kg/ha | Growth height cm | relative |
|---|---|---|---|
| 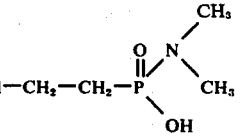 | 6 | 17.0 | 44.7 |
We claim:
1. A compound of the formula
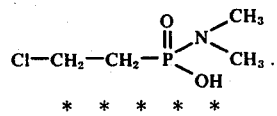
* * * * *